United States Patent
Carter et al.

(10) Patent No.: US 9,983,119 B2
(45) Date of Patent: May 29, 2018

(54) SAMPLE SPINNERS AND SPECTROMETERS INCLUDING SAMPLE SPINNERS

(71) Applicant: PerkinElmer Singapore PTE Ltd., Singapore (SG)

(72) Inventors: Ralph Lance Carter, Thame (GB); David Gosbee, Leighton Buzzard (GB); Julian King, Berkhamsted (GB)

(73) Assignee: PerkinElmer Singapore PTE Limited, Singapore (SG)

( * ) Notice: Subject to any disclaimer, the term of this patent is extended or adjusted under 35 U.S.C. 154(b) by 0 days. days.

(21) Appl. No.: 14/905,691

(22) PCT Filed: Jul. 14, 2014

(86) PCT No.: PCT/GB2014/000285
§ 371 (c)(1),
(2) Date: Jan. 15, 2016

(87) PCT Pub. No.: WO2015/008016
PCT Pub. Date: Jan. 22, 2015

(65) Prior Publication Data
US 2016/0370284 A1    Dec. 22, 2016

(30) Foreign Application Priority Data
Jul. 18, 2013  (GB) .................................. 1312913.5

(51) Int. Cl.
*G01N 21/01* (2006.01)
*G01N 21/03* (2006.01)
(Continued)

(52) U.S. Cl.
CPC ............ *G01N 21/03* (2013.01); *G01J 3/0267* (2013.01); *G01J 3/0291* (2013.01); *G01N 21/47* (2013.01); *G01N 21/57* (2013.01)

(58) Field of Classification Search
CPC ..... G01B 11/026; G01B 11/002; G01B 11/14; G01S 5/163; G01S 5/16
(Continued)

(56) References Cited

U.S. PATENT DOCUMENTS

| 4,902,131 A | 2/1990 | Yamazaki et al. |
| 5,233,923 A * | 8/1993 | Fuchi .................. B41F 13/0045 101/425 |

(Continued)

FOREIGN PATENT DOCUMENTS

| FR | 2638834 A1 | 5/1990 |
| JP | S58140609 A1 | 8/1983 |

(Continued)

OTHER PUBLICATIONS

PerkinElmer Instruction Manual for Near Infared Reflectance Accessory.

*Primary Examiner* — Tarifur Chowdhury
*Assistant Examiner* — Md M Rahman
(74) *Attorney, Agent, or Firm* — Lando & Anastasi, LLP (57) ABSTRACT

A detachable diffuse reflectance spectroscopy sample spinner (2) for use with a spectrometer (1) in diffuse reflectance spectroscopy. The sample spinner (2) comprises a sample receiving turntable (23) mounted for rotation and a motor unit (5) comprising a motor for rotatingly driving the turntable (23). The spinner (2) can comprise wireless electrical power receiver means (54) for receiving electrical power wirelessly for powering the motor (5).

21 Claims, 3 Drawing Sheets

(51) Int. Cl.
  *G01N 21/47* (2006.01)
  *G01N 21/57* (2006.01)
  *G01J 3/02* (2006.01)

(58) Field of Classification Search
  USPC .......................................................... 356/614
  See application file for complete search history.

(56) References Cited

U.S. PATENT DOCUMENTS

| | | | |
|---|---|---|---|
| 5,543,924 A | 8/1996 | Surowiec | |
| 6,419,801 B1 * | 7/2002 | Smith, Jr. | G01J 3/28 204/192.13 |
| 7,053,373 B1 * | 5/2006 | Cleary | G01N 35/025 250/339.07 |
| 7,869,035 B2 | 1/2011 | Bruins | |
| 2003/0233893 A1 * | 12/2003 | Bremer | G01N 30/24 73/864.21 |
| 2005/0094864 A1 | 5/2005 | Xu et al. | |
| 2008/0164776 A1 * | 7/2008 | Yoshimatsu | H01F 41/028 310/90.5 |
| 2010/0027110 A1 | 2/2010 | Ikeda et al. | |
| 2010/0234237 A1 | 9/2010 | Yoo | |
| 2013/0078625 A1 * | 3/2013 | Holmes | G01N 35/0092 435/6.11 |

FOREIGN PATENT DOCUMENTS

| | | |
|---|---|---|
| JP | S61270642 A | 11/1986 |
| JP | 2005164375 A | 6/2005 |
| JP | 2005218376 A | 8/2005 |
| JP | 2005037326 A | 10/2005 |
| WO | 0025110 A1 | 5/2000 |

* cited by examiner

SAMPLE SPINNERS AND SPECTROMETERS INCLUDING SAMPLE SPINNERS

CROSS-REFERENCE TO RELATED APPLICATIONS

This application is a U.S. national phase application and claims the benefit of priority under 35 U.S.C. § 371 of PCT/GB2014/000285, titled SAMPLE SPINNERS AND SPECTROMETERS INCLUDING SAMPLE SPINNERS and filed on Jul. 14, 2014, which in turn claims priority to GB1312913.5, filed on Jul. 18, 2013, the contents of both of which are hereby incorporated herein by reference in their entireties for all purposes.

This invention relates to sample spinners and spectrometers or accessories for spectrometers including sample spinners, all for use in diffuse reflectance spectroscopy.

In the field of reflectance spectroscopy, a light beam is shone onto a sample. The light reflected from the sample is collected and subjected to spectroscopic analysis in order to determine the chemical composition of the sample.

Often the nature or texture of the sample causes it to scatter the reflected light, causing diffuse reflectance.

Generally it is desirable that the illuminated region of the sample is relatively small. For a given size of detector it is possible to collect proportionally more of the total reflected light from a scattering sample when the illuminated region is small. A system that collects more light generally enables measurements of greater sensitivity and precision to be made.

On the other hand, samples which are to be investigated using reflectance spectroscopy are often inhomogenous. This means that the compositional measurement will vary depending on which part of the sample is illuminated. This spatial variation will be worse when the beam is small.

Thus, in at least some circumstances, a spinner or sample spinner is used to move the sample, with respect to the optical system, during measurement so that the results are averaged over a larger area. To put this another way, the use of such a sample spinner means that a larger portion of the sample is actually investigated.

Typically, for convenience, the illuminating beam is directed upwards through a protective window and the sample placed in a transparent bottomed container (for example a petri dish) over the beam. In such a case the container is usually placed on an annular turntable which is positioned such that the beam is incident near the periphery of the unobstructed aperture of the spinner turntable.

A potential disadvantage of such an arrangement is that spillage of material can tend to collect around and under the spinner, including on the protective optical window. Any such material on the window will tend to cause erroneous measurement results and/or spilt material may generally foul the spinner.

Thus it is desirable if it is easy to clean the spinner and the surfaces on which it is located.

Furthermore, drive needs to be provided to the spinner turntable and if there are any detachable components or connections, it is desirable that these are robust and easy to clean.

It is desirable that any connection system is waterproof, dustproof, unobtrusive and easily disconnected.

According to a first aspect of the present invention there is provided a detachable sample spinner for use with a spectrometer in diffuse reflectance spectroscopy, the sample spinner comprising a sample receiving turntable mounted for rotation and a motor unit comprising a motor for rotatingly driving the turntable.

The motor unit may comprise a sealed housing which houses the motor, the turntable being exterior to the sealed housing.

The spinner may comprise magnetically coupled transmission means for transferring drive from the motor to the turntable. This can avoid the use of a drive shaft which penetrates the sealed housing. This in turn means that the motor unit can act as a sealed motor unit with no parts penetrating the housing.

Typically a magnetically coupled transmission means will comprise a spaced pair of rotary parts, a first of which carries a plurality of permanent magnets and a second of which carries a corresponding plurality of permanent magnets or is of magnetic material such that rotation of the first rotary part causes rotation of the second rotary part and vice versa.

The sealed motor unit may be washable. The spinner may be washable.

The turntable may be annular. In an alternative the turntable might have a central window portion.

The spinner may comprise a base portion comprising a bearing surface for supporting the turntable for rotation.

The spinner may comprise a cover portion which covers an outer peripheral portion of the turntable. This can help direct any spilt material away from the bearing surface.

Preferably the turntable has a portion which extends radially inwardly of the bearing surface.

The cover portion may have a generally circular aperture allowing the placing of a sample on the turntable. A peripheral portion of the cover portion surrounding the aperture may be inclined downwardly towards the turntable.

An upper surface of the turntable in a region where this meets or approaches the peripheral portion of the cover portion surrounding its aperture may be chamfered downwardly towards the centre of the turntable.

One or more of the above features can help direct any spilt material away from the bearing surface.

The turntable and cover may be detachably mounted on the base portion. This can aid cleaning.

The magnetically coupled transmission means may comprise a gear wheel mounted for rotation on the base portion and arranged for driving the turntable, and a driver within the housing which is arranged for rotational drive by the motor, the gear wheel being magnetically coupled across a wall of the sealed housing to the driver.

The turntable may comprise a series of teeth which mesh with the gear wheel, to allow transfer of drive.

The sample spinner may comprise a plurality of locating features for locating the sample spinner in a desired position on a spectrometer.

The locating features may comprise at least one projection or recess for mating with a corresponding recess or projection provided on a spectrometer. The locating features may comprise at least one permanent magnet for attraction to a corresponding permanent magnet provided on a spectrometer.

Preferably the locating features on the spinner comprise at least one permanent magnet and at least one projection or recess.

Preferably the locating features on the spinner comprise recesses so that the corresponding features provided on the spectrometer are projections. This will tend to lead to less trapping of any spilt material.

The spinner may comprise wireless electrical power receiver means for receiving electrical power wirelessly for powering the motor.

Preferably the receiver means is provided within the motor unit.

The spinner may comprise a control means which is connected to the motor and the receiver means.

Preferably the control means is provided within the motor unit.

Thus the motor unit can be arranged to have no physical electrical connectors or wires that penetrate the sealed housing.

The spinner may be arranged to draw electrical current via the receiver means independently of operation of the motor.

This can enable a device supplying the power wirelessly to the spinner to detect the presence of the spinner without operation of the motor.

The control means may be arranged to modulate electrical current drawn via the receiver means in order to encode data for extraction by a device supplying the power wirelessly to the spinner.

This can allow data to be transmitted to a device supplying the power wirelessly to the spinner without the need for a separate communications channel. It can also avoid the need for separate sensors or similar.

The data may comprise an indication of a characteristic of the spinner—for example a size, type or serial number.

Such modulation may be carried out independently of operation of the motor in the spinner.

The control means may be arranged to delay starting of the motor for a predetermined period after power has begun to be received via the receiver means.

This can facilitate detection of the presence of the spinner without motor operation and/or facilitate sending of data by modulation of the current drawn by the spinner. Having said this sending of data by modulation of the current drawn by the spinner is possible during motor operation. The device from which current is drawn can be arranged to distinguish data carrying modulations and other variations. The modulation scheme may be chosen to aid distinguishing between data encoding modulations and other variations in current drawn by the spinner.

In an alternative the device supplying power wirelessly to the spinner may be arranged to detect the presence of the spinner without any current being drawn by the spinner.

The control means may be arranged for monitoring the speed of the motor and/or the current drawn by the motor.

The spinner may comprise a indicator for indicating when cleaning of the spinner is required.

The control means may be arranged to determine if cleaning is required by comparing the monitored speed of the motor and the monitored current drawn by the motor. This is on the basis that increased friction in the unit will tend to increase the current drawn by the motor at a given rotational speed, and increased friction can be considered to be indicative of a need to clean the spinner.

The control means may be arranged to activate the indicator in response to a determination that cleaning is required.

The control means may be arranged to determine if at least one of: the motor stalls, the motor malfunctions, the magnetically coupled transmission means fails or slips. The control means may be arranged to deactivate the motor on making such a determination.

According to a second aspect of the present invention there is provided a spectrometer arrangement or spectrometer accessory arrangement, for use in diffuse reflectance spectroscopy comprising a base unit and detachably mounted on the base unit a spinner as defined above.

According to a third aspect of the present invention there is provided a spectrometer or spectrometer accessory, for use in diffuse reflectance spectroscopy, comprising a base unit which is arranged to have detachably mounted thereon, a spinner as defined above.

The base unit may comprise wireless electrical power transmitter means for transmitting electrical power wirelessly to the spinner.

The base unit may comprise a plurality of locating features for locating the sample spinner in a desired position on the base unit.

The locating features on the base unit may comprise at least one projection or recess for mating with a corresponding recess or projection provided on the spinner. The locating features on the base unit may comprise at least one permanent magnet for attraction to a corresponding permanent magnet provided on the spinner.

Preferably the locating features on the base unit comprise at least one permanent magnet and at least one projection or recess.

Preferably the locating features on the base unit comprise projections. This will tend to lead to less trapping of any spilt material.

Preferably the locating features on the base unit comprise a plurality of projections and a plurality of permanent magnets and the locating features on the spinner comprise a plurality of corresponding recesses and a plurality of corresponding permanent magnets, which are in register with the locating features on the base unit. Thus in mounting the spinner on the base unit, the permanent magnets draw the spinner and base unit together and towards a desired relative positioning and the projections and recesses interact for ensuring attainment of the desired relative positioning.

The magnets and projection/recess pairs together serve to positively engage the spinner and base unit in the desired relative positioning.

The base unit may comprise a base unit control means which is connected to the transmitter means.

The base unit control means may be arranged to monitor the current transmitted by the transmitter means.

The base unit control means may be arranged to monitor the power consumed by the system.

The base unit control means may be arranged to detect the presence of a device, for example, a spinner mounted on the base unit.

The base unit control means may be arranged to detect the presence of a spinner mounted on the base unit in dependence on the current transmitted by the transmitter means.

The base unit control means may be arranged to extract data by monitoring the current transmitted by the transmitter means where the current is modulated. This will be the case where a spinner mounted on the base unit modulates the electrical current drawn via the wireless power transmission system to encode data.

The base unit control means may be arranged to distinguish between modulations in the electrical current drawn which are due to data encoded by the spinner and other variations in the current drawn. The other variations may be due to changes on the load on the motor, for example. The modulation used by the spinner to encode data may be chosen to aid in distinguishing the data encoding modulations from other variations in current drawn by the spinner. The base unit control means may include filter means for use in distinguishing between data encoding modulations and other variations.

The spectrometer arrangement or spectrometer accessory arrangement may comprise a indicator for indicating when cleaning of the spinner is required.

The base unit may comprise a indicator for indicating when cleaning of the spinner is required.

The spectrometer arrangement or spectrometer accessory arrangement may be arranged to determine if cleaning is required by comparing the monitored speed of the motor and the monitored current drawn by the motor.

The base unit control means may be arranged to determine if cleaning is required by comparing the monitored speed of the motor and the monitored current drawn by the motor. This is on the basis that increased friction in the unit will tend to increase the current drawn by the motor at a given rotational speed, and increased friction can be considered to be indicative of a need to clean the spinner.

The spectrometer arrangement or spectrometer accessory arrangement may be arranged to activate the indicator in response to a determination that cleaning is required.

The base unit control means may be arranged to activate the indicator in response to a determination that cleaning is required.

The spectrometer arrangement or spectrometer accessory arrangement may be arranged to determine if at least one of: the motor stalls, the motor malfunctions, the magnetically coupled transmission means fails or slips. The spectrometer arrangement or spectrometer accessory arrangement may be arranged to deactivate the motor on making such a determination. The spectrometer arrangement or spectrometer accessory arrangement may be arranged to indicate an error has occurred on making such a determination.

The base unit control means may be arranged to determine if at least one of: the motor stalls, the motor malfunctions, the magnetically coupled transmission means fails or slips. The base unit control means may be arranged to deactivate the motor on making such a determination. The base unit control means may be arranged to indicate an error has occurred on making such a determination.

All the optional features following the first aspect of the invention can also be optional features of the second and third aspects of the invention, with any necessary changes in wording being made—they are not repeated here in the interests of brevity.

According to a fourth aspect of the present invention there is provided a method of carrying out diffuse reflectance spectroscopy using a spinner as defined above comprising the steps of placing a sample on the spinner, operating the spinner to cause the sample to rotate and taking diffuse reflectance spectroscopy measurements whilst the sample is rotating.

All the optional features following the first to third aspects of the invention can also be optional features of the fourth aspect of the invention, with any necessary changes in wording being made—they are not repeated here in the interests of brevity.

Embodiments of the present invention will now be described, by way of example only, with reference to the accompanying drawings, in which.

Figure 1:
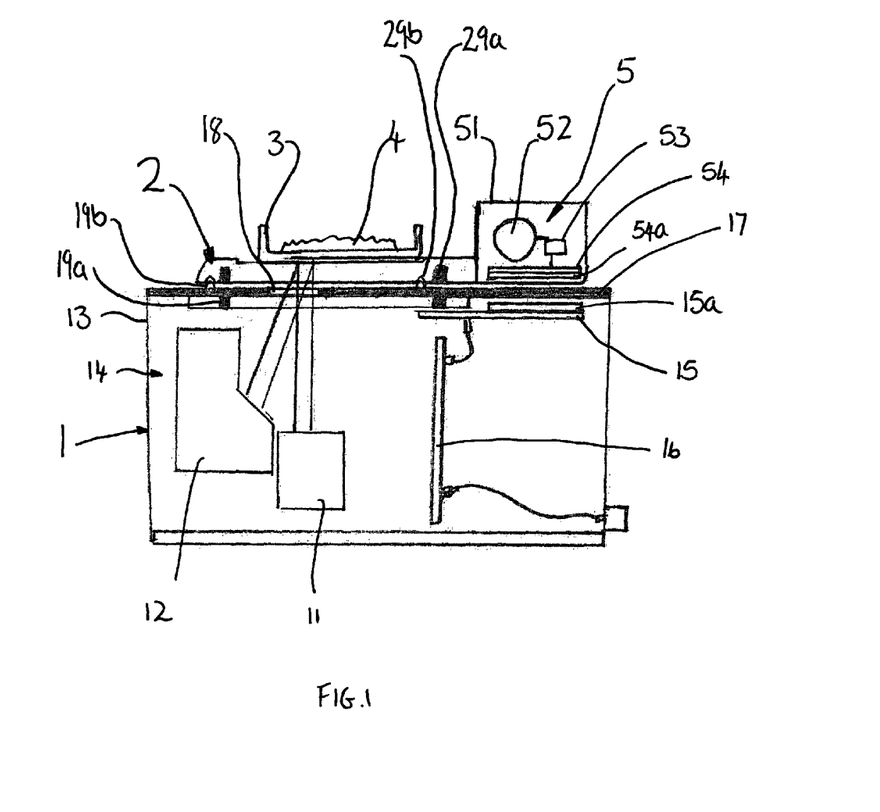
FIG. 1 schematically shows a spectrometer arrangement, including a sample spinner.

FIG. 1 schematically shows a spectrometer arrangement comprising a spectrometer 1 on which is mounted a sample spinner 2 which is shown carrying a petri dish 3 in which is located a sample 4 for investigation.

The general principles of diffuse reflectance spectroscopy are well understood and these will not be described in detail in this specification. However, a very brief description of the process follows.

The spectrometer comprises illumination optics 11 and detection optics 12 together with an appropriate analysis module (not shown). In operation the illumination optics 11 direct an illumination beam towards the sample 4. This undergoes diffuse reflectance at the sample 4 and the reflected beam is gathered by the detection optics 12. This process is continued for a predetermined period of time whilst the sample spinner 2 rotates the sample 4, causing different portions of the sample 4 to be illuminated by the illumination optics and hence to cause different portions of the sample to reflect light towards the detection optics 12.

The detection optics 12 and associated analysis module (not shown) can then analyse the spectrum of the received reflected beam, and using known techniques it is possible to determine information concerning the composition of the sample 4. In the present embodiment the spectrometer is an FT-IR (Fourier Transform-Infra Red) spectrometer. Again, the use of FT-IR spectrometers in diffuse reflectance spectroscopy for determining the composition of samples is well understood and the details of its operation are not particularly pertinent to the present invention, and thus no further description is given here. The sample spinner can be considered a reflectance spectroscopy sample spinner or more particularly still a FT-IR reflectance spectroscopy sample spinner.

The present specification is concerned with the structure and operation of the sample spinner 2 as well as its interaction with various features of the spectrometer 1. More details of these features will now be described below.

The spectrometer 1 comprises a housing 13 which can be considered to define a base unit 14 of the spectrometer 1 in the present embodiment.

Note that in other embodiments the base unit may form part of a spectrometer accessory which is used with a slightly differently constituted spectrometer. In such an implementation there may be a main spectrometer body, which is arranged to accept at least one type of accessory, and in practice many different types of accessory, for performing different functions. In such an accessory based implementation, at least part of the illumination optics 11 and/or detection optics 12 and analysis module would likely be provided within the spectrometer main body rather than the accessory. However parts specific to the present techniques would most likely be provided in the accessory. In either implementation there will be a base unit 14 with parts specific to the present techniques.

The base unit 14 also comprises a wireless electrical power transmission module 15 (including a transmitter coil 15a) and a control unit 16 which is connected to the transmission module 15. The base unit 14 has an upper surface 17 which is arranged for receiving the spinner 2. The upper surface 17 is substantially flat and furthermore is as free from projections and recesses and so on as is possible. This is to avoid trapping of material and to ensure that this upper surface 17 is as easy to clean as possible.

An illumination and detection window 18 is provided in the upper surface 17 through which the illumination beam and reflected beam pass before and after reflection by the sample 4.

A series of locating features 19a, 19b are provided in the region of the upper surface 17. These comprise a series of permanent magnets 19a provided just below the upper surface 17 and a series of projections 19b provided on the surface 17. In the present embodiment these projections 19b have a part spherical surface, in particular the projections are formed of the upper third of a sphere projecting above the surface 17. The locating features 19a, 19b are for use in locating the spinner 2 on the base unit 14 as will be described in more detail below.

Figure 2:
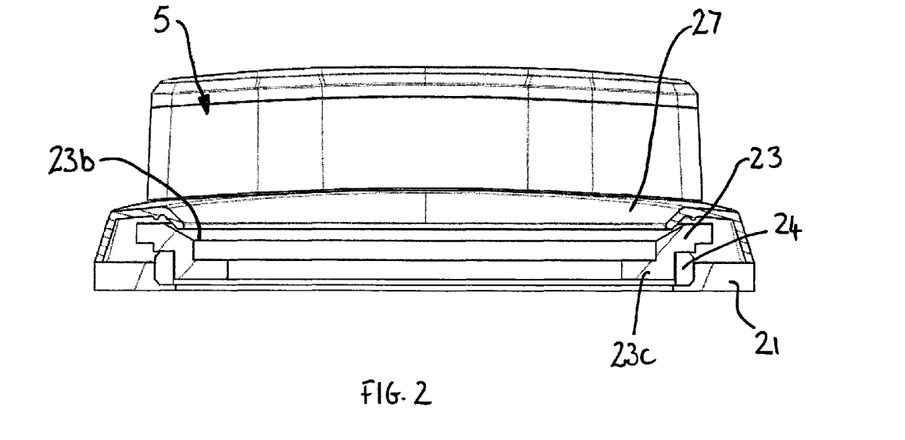
FIG. 2 is a sectional view showing the sample spinner of the spectrometer arrangement of FIG. 1 in more detail.
Figure 3:
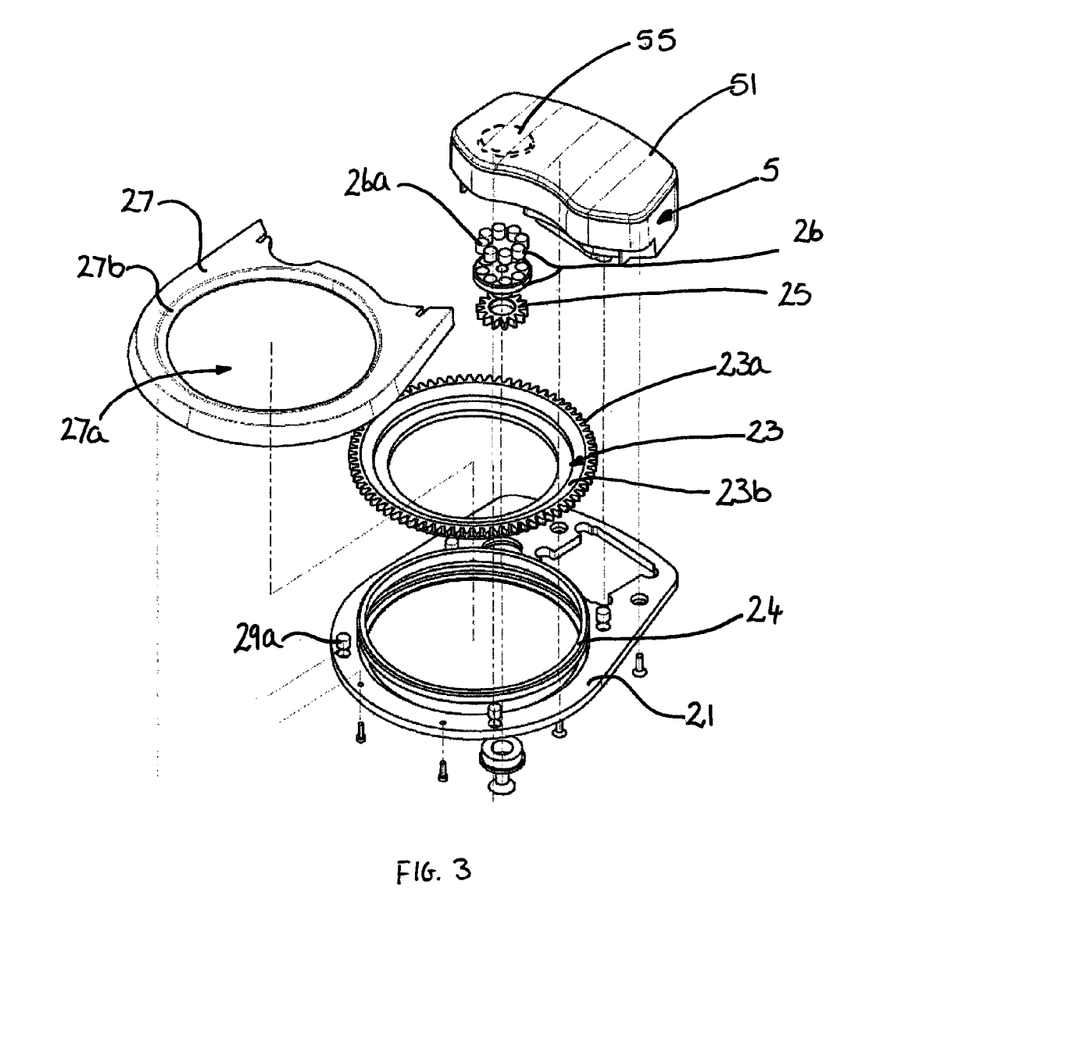
FIG. 3 is an exploded view of the sample spinner shown in FIG. 2.

Referring to FIGS. 1, 2 and 3 the spinner comprises a base plate 21 on which is mounted a motor unit 5 and an annular turntable 23 which is arranged to accept a sample 4, for example a sample 4 carrying petri dish 3, as shown in FIG. 1. The annular turntable 23 is mounted for rotation relative to the baseplate 21 on a bearing surface 24. A drive gear 25 is mounted for rotation on the base plate 23 and has fixed thereto a coupling portion 26 which is one half of a rotational magnetic coupling. The coupling portion 26 includes a plurality of permanent magnets 26a and is shown in exploded form in FIG. 3. The magnetic coupling portion 26 and drive gear 25 are mounted for rotation on the base plate 21 with the gear wheel 25 meshing with teeth 23a on the outer periphery of the turntable 23, such that rotation of the coupling portion 26 and gear wheel 25 causes rotation of the turntable 23.

The motor unit 5 comprises a sealed housing 51 within which the other parts of the motor unit are contained. Note that no parts penetrate through the walls of this sealed housing 51. In particular there is no drive shaft which penetrates through the housing 51. This is because a magnetically coupled drive is used to transfer drive across the wall of the housing 51 as will be described in more detail below.

A cover 27 with a main central circular aperture 27a is provided to cover an outer periphery of the turntable 23, including the teeth 23a.

As can be seen by considering FIGS. 2 and 3 the cover 27 comprises a downwardly inclined portion 27b around the periphery of the aperture 27a. This tends to direct any spilt material towards the turntable and the centre of the turntable 23 away from the bearing portion 24 and driving mechanism 23a, 25. Further, an upper portion of the turntable 23 in the region where the inclined portion 27b of the cover 27 meets the turntable 23 is chamfered to provide a chamfered surface 23b, which is inclined downwardly towards the centre of the turntable 23. Again this surface tends to direct any spilt material away from the bearing surface 24 and the driving mechanism 23a, 25.

The turntable 23 has a portion 23c which extends radially inwardly of the bearing surface 24 and the cover portion 27 covers the external periphery of the turntable 23. Further the portion 23c which is radially inward of the bearing surface 24 projects down below the level of at least an axial portion of the bearing surface 24. This all helps to keep split material away from the bearing surface 24 and drive mechanism 23a, 25.

The cover portion 27 and turntable 23 are easily removeable from the base plate 21 to allow cleaning. Thus these parts may be individually washed before reassembly onto the base plate 21. Furthermore because the motor unit 5 is a sealed unit this may also be washed. This may be washed when mounted in situ on the base plate 21 or removed from the base plate for even more thorough cleaning. Similarly the gear wheel 25 and coupling portion 26 may be retained mounted to the based plate 21 for cleaning or fully disassembled for more complete cleaning.

If desired, the whole spinner 2 may be held under a running tap in order to clean sample spillages off of the spinner.

Within the housing 51, the motor unit 5 comprises a motor 52 which is connected to a control unit 53. In turn connected to the control unit 53 is a wireless electrical power receiver module 54 including a receiver coil 54a. The motor 52 is arranged to rotationally drive a driver 55 (see FIG. 3) which acts as part of the magnetic coupling across the wall of the housing 51. The driver 55 is arranged for alignment with the magnetic coupling portion 26 which is mounted for rotation on the base plate 21, such that rotation of the driver 55 under operation of the motor 52 causes the magnetic coupling portion 26 to rotate so rotating the drive wheel 25 and hence the turntable 23. As such the driver 55 and coupling portion 26 form a rotational magnetic coupling.

As described above in relation to FIG. 3, the magnetic coupling portion 26, mounted on the base plate 21, includes a plurality of permanent magnets 26a. The driver 55 within the motor unit 5 comprises a corresponding set of permanent magnets (not shown) to ensure good magnetic coupling between the driver 55 and the magnetic coupling portion 26.

The base plate 21 carries a plurality of permanent magnets 29a and a plurality of recesses 29b to act as locating features when the spinner 22 is located on the upper surface 17 of the base unit 14. The arrangement of the permanent magnets 29a on the spinner 2 is arranged to register with the corresponding arrangement of magnets 19a provided in the base unit 14 so that as the spinner 2 is put onto the upper surface 17 of the base unit, the magnets 19a, 29a, tend to draw the spinner 2 towards the base unit 14 and towards a desired location for the spinner 2 on the base unit 14. Furthermore the recesses 29b provided in the underside of the base plate 21 are arranged to interact with the projections 19b provided on the upper surface 17 of the base unit 14 so as to locate the spinner 2 in a desired position on the base unit 14 as it is brought into position. In the present embodiment the recesses 29b are conical recesses and are dimensioned to accept the part spherical projections 19b.

The magnets 29a, 19a together with the projections 19b and recesses 29b, serve to positively and accurately engage and locate the spinner 2 on top of the spectrometer 1.

The magnets 19a, 29a provide good initial lateral location as well as drawing the parts together. On the other hand the projections 19b and recesses 29b serve to provide a more accurate and definite final lateral location of the spinner 2 on the spectrometer 1 than the magnets 19a, 29a would alone.

As mentioned above, the base unit 14 of the spectrometer 1 comprises a wireless electrical power transmitter module 15 and the spinner 2 comprises a wireless electrical power receiver module 54.

Thus the system is arranged so that in use electrical power is wirelessly transmitted from the base unit 14 to the spinner 2, in particular to the motor unit 5, to allow operation of the motor 52 so causing rotation of the turntable 23. When the transmitter module 15 energises the transmitter coil 15a an alternating magnetic field is generated which in turn induces a corresponding electrical current in the receiver coil 54a so transmitting power from the base unit 14 to the motor unit 5. This allows a physical connectorless detachable arrangement between the base unit 14 and the spinner 2 which simplifies use and aids cleaning.

Accurate locating of the spinner 2 on the base unit 14 is helpful for ensuring efficiency in transfer of electrical power from the base unit 14 to the motor unit 5. Similarly accurate positioning of the spinner 2 on the base unit 14 is useful for ensuring that the illumination optics 11 and detection optics 12 direct light to and collect light from an appropriate portion of a carried sample 4.

The control unit 53 in the motor unit 5 is arranged for monitoring the current drawn by the motor 52 and also the speed of rotation of the motor 52. The speed of rotation of the motor is sensed using Hall sensors (not shown) which are built into the motor 52.

The motor unit 5 includes an indicator (not shown), for example an LED, which the control unit 53 is arranged to operate, e.g. light up, if the amount of current drawn by the motor 52 exceeds that expected for a given speed. This is on the basis that the fact that more current is being drawn than is expected is indicative of increased friction in the drive of the turntable 23, which in turn suggests that cleaning is required.

The control unit 53 is also arranged to detect if the motor 52 stalls or the magnetic coupling between the driver 55 and coupling portion 26 slips. If such a condition is detected the control unit 53 is arranged to shut down the motor 52.

The motor unit 5, in particular the control unit 53 and receiver module 54, are arranged such that when electrical power is initially received by the receiver module 54, there is a delay before operation of the motor 52.

This helps enable operation of a spinner 2 presence detection function of the base unit 14.

That is to say the base unit 14 is arranged to momentarily send power to the transmitter module 15 and sense whether any current is drawn. The drawing of current indicates that a spinner 2 is present on the base unit 14. The transmitter module 15 may then be shut down by the base unit control unit 16 before the motor 52 has started to operate. That is to say the transmission of power may be stopped in less time than the delay which the spinner 2 is arranged to use. In this way it is possible for the base unit 14 to detect the presence of a spinner 2 without operating the motor 52. This means that the presence of the spinner 2 may be detected without alerting or disconcerting a user due to any unrequested operation of the motor 52 and hence turntable 23.

In a further development of such functionality the control unit 53 of the spinner is arranged to draw a small modulated amount of current. This current may be drawn during the initial period before motor operation, as mentioned above and/or during motor operation. The drawing of this current is independent of motor operation.

The spinner control unit 53 is arranged to modulate the current drawn in order to encode data. In particular, the control unit 53 may encode data indicating a characteristic of the spinner 2. This might be a size of the spinner, a size of the turntable of the spinner, a serial number, or indeed some other data which is to be transmitted to the base unit 14.

The control unit 16 of the base unit 14 is arranged to monitor the current drawn by the spinner and where the current is modulated, the base unit control unit 16 is arranged to extract data from the modulated drawn current so as to extract the data encoded by the spinner 2. This can enable the base unit 14 to act accordingly under the control of the control unit 16, based on the characteristic information of the spinner 2 or other data transmitted by the spinner 2.

Thus, for example, the base unit 14 may be configured to recognise when a spinner 2 having a particular size of turntable is present on the unit and make any necessary changes to the operation of the base unit 14 accordingly. This may include selecting a different set of parameters for the supply of electrical power or expected current versus speed characteristics.

The above features can avoid the need for any sensors or secondary wireless communication links to convey information to the base unit about the presence of a spinner 2 and/or characteristics of the spinner 2.

Note that in the present embodiment the control unit 16 of the base unit 14 is arranged to distinguish between data carrying modulations and other variations in the current drawn. This is achievable in various ways. Further, the modulation scheme used by the spinner 2 may be chosen to aid in this distinguishing capability.

In the present case a frequency band is allocated for data transmission and the control unit includes filter means to filter out signals outside this band. The filter means may be physical or implemented in signal processing. In the present embodiment the frequency band for data transmission is chosen so as to be away from other known current modulations such as that caused by the motor, bearing, gears etc, slipping in magnetic coupling, and any modulations used in wireless power regulation. Modulations due to the physical factors above may for example all be sub 20 Hz and that used in wireless power regulation may be greater than 1 KHz. In such a case the band for transmission of data may be say 50 Hz to 300 Hz and a band pass filter may be used with the appropriate frequency characteristics to cut out signals outside this band.

The invention claimed is:

1. A detachable diffuse reflectance spectroscopy sample spinner for use with a spectrometer in diffuse reflectance spectroscopy, the sample spinner comprising:
   a sample receiving turntable mounted for rotation;
   a motor unit comprising a motor for rotatingly driving the turntable; and
   a wireless electrical power receiver for receiving electrical power wirelessly for powering the motor,
   wherein the sample spinner comprises a plurality of locating features for locating the sample spinner in a desired position on the spectrometer, the plurality of locating features comprising at least one projection or recess for mating with a corresponding recess or projection provided on the spectrometer, and the plurality of locating features comprising at least one permanent magnet for attraction to a corresponding permanent magnet provided on the spectrometer.

2. The detachable sample spinner according to claim 1 in which the sample spinner is arranged to draw an electrical current via the receiver independently of motor operation.

3. The detachable sample spinner according to claim 1 in which the sample spinner is arranged to modulate electrical current drawn via the receiver in order to encode data for extraction by a device supplying the power wirelessly to the sample spinner.

4. The detachable sample spinner according to claim 1 in which the sample spinner is arranged to delay starting of the motor for a predetermined period after power has begun to be received via the receiver.

5. The detachable sample spinner according to claim 1 in which the sample spinner is arranged for monitoring a speed of the motor and a current drawn by the motor, and in which the sample spinner is arranged to determine if cleaning is required by comparing the monitored speed of the motor and the monitored current drawn by the motor.

6. The detachable sample spinner according to claim 1 in which the motor unit comprises a sealed housing which houses the motor, the turntable being exterior to the sealed housing.

7. The detachable sample spinner according to claim 1 in which the sample spinner comprises a magnetically coupled transmission arrangement for transferring drive from the motor to the turntable.

8. The detachable sample spinner according to claim 1 in which the sample spinner comprises a base portion comprising a bearing surface for supporting the turntable for rotation, and a cover portion which covers an outer peripheral portion of the turntable.

9. A spectrometer arrangement or spectrometer accessory arrangement, for use in the diffuse reflectance spectroscopy, comprising a base unit and detachably mounted on the base unit the sample spinner according to claim 1.

10. The spectrometer arrangement or spectrometer accessory arrangement according to claim 9 in which the base unit comprises a wireless electrical power transmitter for transmitting electrical power wirelessly to the sample spinner.

11. The spectrometer arrangement or spectrometer accessory arrangement according to claim 10 comprising base unit control means which are arranged to detect a presence of a sample spinner mounted on the base unit in dependence on a current transmitted by the power transmitter.

12. The spectrometer arrangement or spectrometer accessory arrangement according to claim 10 comprising base unit control means which are arranged to extract data sent by the sample spinner by monitoring a current transmitted by the power transmitter.

13. The spectrometer arrangement or spectrometer accessory arrangement according to claim 9 in which the base unit comprises a plurality of locating features for locating the sample spinner in a desired position on the base unit.

14. The spectrometer arrangement or spectrometer accessory arrangement according to claim 9 in which the base unit comprises wireless electrical power transmitter means for transmitting electrical power wirelessly to the sample spinner.

15. A spectrometer or spectrometer accessory, for use in diffuse reflectance spectroscopy, comprising a base unit which is arranged to have detachably mounted thereon, a sample spinner according to claim 1.

16. The detachable sample spinner according to claim 1 in which the sample spinner comprises wireless electrical power receiver means for receiving electrical power wirelessly for powering the motor.

17. The detachable sample spinner according to claim 1 in which the sample spinner comprises magnetically coupled transmission means for transferring drive from the motor to the turntable.

18. A detachable diffuse reflectance spectroscopy sample spinner for use with a spectrometer in diffuse reflectance spectroscopy, the sample spinner comprising:
a sample receiving turntable mounted for rotation;
a motor unit comprising a motor for rotatingly driving the turntable;
a wireless electrical power receiver for receiving electrical power wirelessly for powering the motor;
a base portion comprising a bearing surface for supporting the turntable for rotation; and
a cover portion which covers an outer peripheral portion of the turntable,
wherein the turntable has a portion which extends radially inwardly of the bearing surface, the cover portion has a generally circular aperture allowing the placing of a sample on the turntable with a peripheral portion of the cover portion surrounding the aperture being inclined downwardly towards the turntable, wherein an upper surface of the turntable in a region where the upper surface of the turntable meets or approaches the peripheral portion of the cover portion surrounding the aperture of the cover portion is chamfered downwardly towards a centre of the turntable.

19. A spectrometer arrangement or spectrometer accessory arrangement, for use in diffuse reflectance spectroscopy, comprising:
a base unit; and
a sample spinner detachably mounted on the base unit, the sample spinner including
a sample receiving turntable mounted for rotation;
a motor unit comprising a motor for rotatingly driving the turntable; and
a wireless electrical power receiver for receiving electrical power wirelessly for powering the motor,
wherein the base unit comprises a plurality of locating features for locating the sample spinner in a desired position on the base unit, and
wherein the plurality of locating features on the base unit comprise a plurality of projections and a plurality of permanent magnets and the plurality of locating features on the sample spinner comprise a plurality of corresponding recesses and a plurality of corresponding permanent magnets, which are in register with the plurality of locating features on the base unit.

20. A detachable diffuse reflectance spectroscopy sample spinner for use with a spectrometer in diffuse reflectance spectroscopy, the sample spinner comprising:
a sample receiving turntable mounted for rotation;
a motor unit comprising a motor for rotatingly driving the turntable; and
a plurality of locating features for locating the sample spinner in a desired position on the spectrometer, the plurality of locating features comprising at least one projection or recess for mating with a corresponding recess or projection provided on the spectrometer, and the plurality of locating features comprising at least one permanent magnet for attraction to a corresponding permanent magnet provided on the spectrometer.

21. A detachable diffuse reflectance spectroscopy sample spinner for use with a spectrometer in diffuse reflectance spectroscopy, the sample spinner comprising:
a sample receiving turntable mounted for rotation;
a motor unit comprising a motor for rotatingly driving the turntable;
a base portion comprising a bearing surface for supporting the turntable for rotation; and
a cover portion which covers an outer peripheral portion of the turntable,
wherein:
the turntable has a portion which extends radially inwardly of the bearing surface,
the cover portion has a generally circular aperture allowing the placing of a sample on the turntable with a peripheral portion of the cover portion surrounding the aperture being inclined downwardly towards the turntable, and
an upper surface of the turntable in a region where the upper surface of the turntable meets or approaches the peripheral portion of the cover portion surrounding the aperture of the cover portion is chamfered downwardly towards a centre of the turntable.

* * * * *